United States Patent [19]

Treiber

[11] Patent Number: 4,916,239

[45] Date of Patent: Apr. 10, 1990

[54] PROCESS FOR THE LACTONIZATION OF MEVINIC ACIDS AND ANALOGS THEREOF

[75] Inventor: Laszlo R. Treiber, Gillette, N.J.

[73] Assignee: Merck & Co., Inc., Rahway, N.J.

[21] Appl. No.: 221,475

[22] Filed: Jul. 19, 1988

[51] Int. Cl.$^4$ ............................................ C07D 309/30
[52] U.S. Cl. .................................................... 549/292
[58] Field of Search ......................................... 549/292

[56] References Cited

U.S. PATENT DOCUMENTS

| | | | |
|---|---|---|---|
| 4,582,915 | 4/1986 | Sletzinger et al. | 549/292 |
| 4,611,067 | 9/1986 | Volante et al. | 549/292 |
| 4,611,068 | 9/1986 | Guindon et al. | 549/292 |

Primary Examiner—Richard L. Raymond
Assistant Examiner—Amelia A. Owens
Attorney, Agent, or Firm—Melvin Winokur; Joseph F. DiPrima

[57] ABSTRACT

A process for the lactonization of mevinic acid HMG-CoA reductase inhibitors and analogs thereof is disclosed.

11 Claims, No Drawings

PROCESS FOR THE LACTONIZATION OF MEVINIC ACIDS AND ANALOGS THEREOF

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

Mevacor ® (lovastatin), now commercially available, is one of a group of very active antihypercholesterolemic agents that function by limiting cholesterol biosynthesis by inhibiting the enzyme, HMG-CoA reductase. In addition to the natural fermentation products, mevastatin and lovastatin, there are a variety of semi-synthetic and totally synthetic analogs thereof.

The naturally occurring compounds and their semi-synthetic analogs have the following general structural formulae:

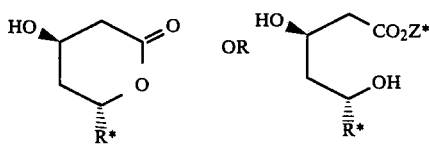

wherein:
Z* is hydrogen, $C_{1-5}$ alkyl or $C_{1-5}$ alkyl substituted with a member of the group consisting of phenyl, dimethylamino, or acetylamino; and
R* is:

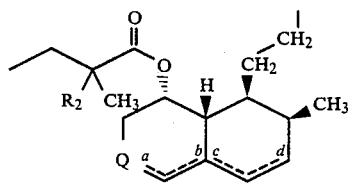

wherein Q is

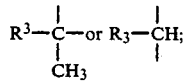

$R^3$ is H or OH; and
$R^2$ is hydrogen or methyl; and a, b, c, and d represent optional double bonds, especially where b and d represent double bonds or a, b, c, and d are all single bonds, provided that when a is a double bond, Q is

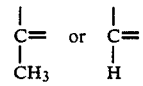

The preparation of the naturally occurring compounds and their semi-synthetic analogs leads to a mixture of the lactone and dihydroxy acid forms. Mevacor ® is marketed in the lactone form and thus it is of considerable importance to employ a high yield efficient method for the lactonization of the free acid or salt form. In the past, lactonization of the free acid or ammonium salt was effected by heating these substrates in a neutral organic solvent such as toluene, ethyl acetate, or isopropyl acetate at or near reflux. The lactonization is catalyzed by the presence of acid. The necessary acidity arises either through the ambient acidity of the substrate itself or by the addition of a stonger acid to effect lactonization at a lower temperature.

Lactonization is an equilibrium process, and in order to obtain a high yield of the lactone product, some means must be employed to shift the equilibrium to the lactone side of the equation:

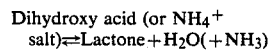

In the prior procedures, lactonization is forced to near completion by removing the reaction by-products (water, ammonia) from the reaction mixture by means of azeotropic distillation and/or nitrogen sweep. The removal of water, and in the case of the ammonium salt ammonia, shifts the position of equilibrium to the lactone side.

Prior lactonization procedures exhibited several disadvantages. Typically the hydroxy acid substrate acted as the acid catalyst and thus as the substrate was consumed, the rate of reaction decreased requiring longer reaction times and allowing for increased by-product formation. Under the reaction conditions, the product 3-hydroxylactone is exposed for prolonged periods of time to the free acid which leads to increased amounts of a dimer (1) which results from an esterification reaction between the 3-hydroxyl group of the 3-hydroxylactone and the free acid.

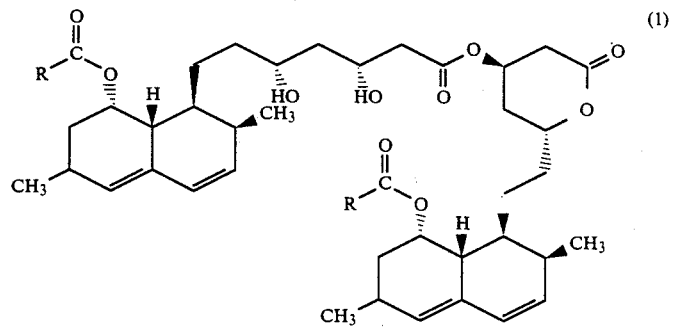

The above dimer impurity has proved to be difficult to separate from the desired lactone product even with careful recrystallization techniques. The presence of the dimer, of course, lowers the overall yield and purity of the lactone product. Efforts to minimize the formation of the dimer have led to the use of high dilution in the lactonization reaction, however, this technique compromises the efficiency of the reaction.

A second impurity, resulting from dehydration of the 3-hydroxyl group on the lactone ring, was also observed using prior lactonization conditions. This impurity was likewise only inefficiently removed by recrystallization, resulting in diminished yields. The present invention alleviates this problem.

DETAILED DESCRIPTION OF THE INVENTION

The instant invention relates to a novel process for the conversion of mevinic acid HMG-CoA reductase inhibitors or analogs thereof into a lactone. The present process enables the shifting of the lactonization equilibrium by the continuous and selective removal of the lactone product from the reaction mixture. To employ this novel approach in the present lactonization equilibrium, it was necessary to identify a reaction medium in which the lactone product would be less soluble than the unlactonized starting material; and find a selective crystallization method for the removal of the lactone without entrainment of process impurities or starting material.

Specifically the instant invention involves treating the free hydroxy acid or ammonium or metal salt derivative of a mevinic acid or analog thereof in an acetic acid medium, or other water miscible organic solvent which exhibits a sufficient solubility difference between the hydroxy acid and lactone, and a strong acid catalyst. After the free hydroxy acid-lactone equilibrium is established, water is gradually added in an amount sufficient to effect complete crystallization of the lactone from the reaction medium. This removal of the lactone continuously shifts the equilibrium to the lactone side and thus drives the lactonization to completion. In the instant procedure, the lactone is continuously removed from the reaction medium as it is formed, minimizing the lactone's exposure to the reaction conditions and thus minimizing the potential for its further reaction to form dimers. Thus one obtains a lactone product free from the impurities complicating the prior art lactonization procedures. The instant invention can be depicted as:

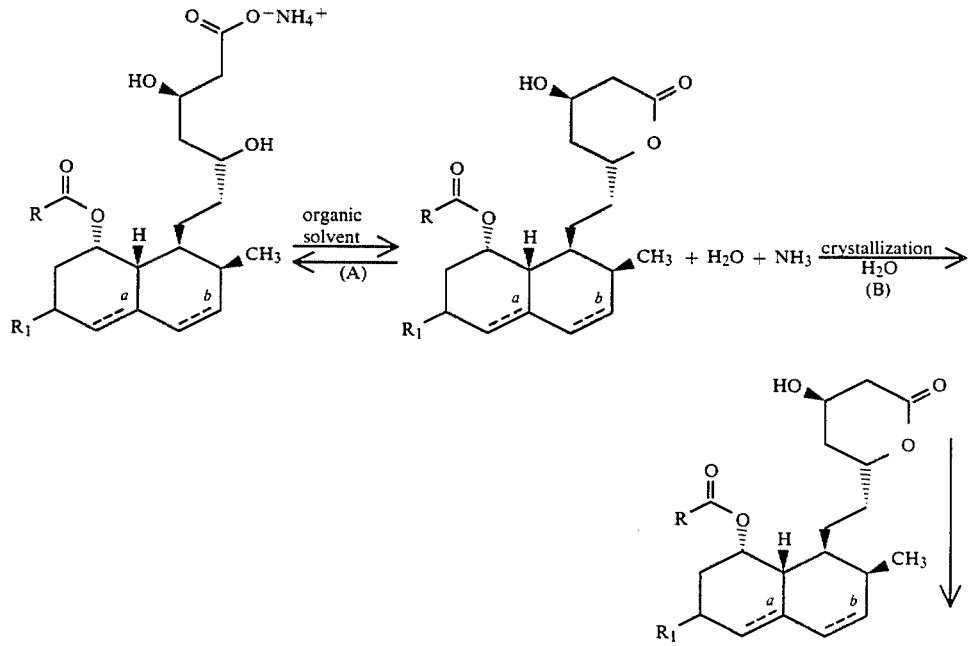

wherein
R is $C_{1-10}$ alkyl;
$R_1$ is $CH_3$, $CH_2OH$,

$CO_2R_3$

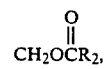
$CH_2OCR_2$,

$CNR_4R_5$,

OH, $CH_2OR_2$ or $CH_2NR_4R_5$;
$R_2$ is $C_{1-5}$ alkyl;
$R_3$ is H or $C_{1-5}$ alkyl;
$R_4$ and $R_5$ are independently selected from H or $C_{1-10}$ alkyl;
a and b are both double bonds or one of a and b is a single bond or both a and b are single bonds.

Major advantages realized in the instant invention compared to the prior art are increased process productivity and product purity. The prior art procedures are conducted in a highly dilute medium (0.1 M) in order to minimize dimer formation. The instant invention allows for lactonization at much higher concentrations (~0.24 M) thus markedly improving productivity. Furthermore, the prior art procedure requires an additional step wherein the solvent is concentrated prior to isolation of the lactone; in the present procedure the lactone is isolated directly from the reaction mixture. Again the instant procedure demonstrates a greater efficiency than the prior art.

With respect to product purity, the prior art method yielded a semi-pure product which contained from 0.4 to 0.8% of a difficult-to-remove dimeric impurity, whereas the levels of this impurity under the-present lactonization conditions is reduced to less than 0.2%.

The specific hydroxy acids or salts derived therefrom, which are employed in the instant invention, are of stucture (I):

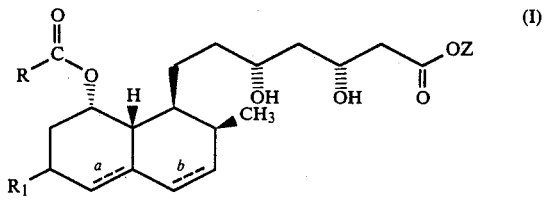

wherein:
R is $C_{1-10}$ alkyl;
$R_1$ is $CH_3$, $CH_2OH$,

$CO_2R_3$, $$\underset{O}{\overset{CNR_4R_5}{\|}}$$

OH, $CH_2OR_2$, or $CH_2NR_4R_5$;
Z is H or $NH_4+$ or a metal cation;
$R_2$ is $C_{1-5}$ alkyl;
$R_3$ is H or $C_{1-5}$ alkyl;
$R_4$ and $R_5$ are independently selected from H or $C_{1-5}$ alkyl; a and b are both double bonds or one of a and b is a single bond or both a and b are single bonds.

The solvents employed are water miscible organic solvents. The particular solvent is determined by the characteristics of crystallization, i.e. the solubility difference between the hydroxy acid or salt and the lactone, the crystallization selectivity and the kinetics of crystallization, in the water-organic solvent mixture. Suitable solvents include acetic acid, acetonitrile, acetone and methanol preferably acetic acid, acetonitrile or acetone.

The rate of lactonization depends on the strength and concentration of the acid catalyst. Any inorganic or organic acid of acidity sufficient to catalyze the formation of a lactone may be employed. Illustrative of suitable acids which may be employed are formic, phosphoric, trifluoroacetic, sulfuric, hydrochloric, perchloric, p-toluenesulfonic and methanesulfonic acid.

The lactonization may e conducted over a temperature range of 20° C. to 30° C., preferably 20°-25° C. It is critical that the temperature not be allowed to rise above 30° C. as this leads to increased by-product formation.

Preferred metal cations are cations of alkali metals, such as sodium or potassium, cations of alkaline earth metals, such as calcium or magnesium, or cations of other metals such as aluminum, iron, zinc, copper, nickel or cobalt. The alkali metal cations, alkaline earth metal cations, and aluminum cations are preferred; the sodium, calcium and aluminum cations being most preferred.

In one embodiment of the instant process is the compounds of formula (I) wherein:
R is $C_{1-10}$ alkyl,
$R_1$ is $CH_3$; and
Z is H+ or $NH_4+$.

In one class of this embodiment, R is sec-butyl or 1,1-dimethylpropyl and $R_1$ is $CH_3$, Z is $NH_4+$, a and b are double bonds, the organic solvent is acetic acid, acetonitrile or acetone and the acid catalyst is trifluoracetic acid or methanesulfonic acid. In one subclass R is 1,1-dimethylpropyl, the organic solvent is acetic acid and the acid catalyst is trifluoracetic or methanesulfonic acid preferably methanesulfonic acid. In a second subclass, R is sec-butyl, the organic solvent is acetone, acetic acid or acetonitrile, and the acid catalyst is trifluoracetic acid or methanesulfonic acid.

The following examples illustrate the process of the instant invention and are not to be considered as limiting the invention set forth in the claims appended hereto.

EXAMPLE 1

Preparation of 6(R)-[2-[8(S)-(2,2-dimethylbutyryloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one Ammonium 7-[1,2,6,7,8,8a(R)-hexahydro-2(S), 6(R)-dimethyl-8(S)-(2,2-dimethylbutyryloxy)-1(S)-naphthyl]-3(R),5(R)-dihydroxyheptanoate (12.5 grams, 97.9 wt. % purity by HPLC, 27.0 mmol) was stirred with a mixture of acetic acid (40 ml), water (20 ml) and trifluoroacetic acid (3.84 g, 33.7 mmol, 2.5 ml) under a nitrogen atmosphere for 3 hours at 23°-26° C.

After the 3 hour age period, the first portion of water (10 ml) was added at once. From that point on, the addition of the second portion of water (15 ml) was carried out uniformly over a period of 3 hours. The product lactone began crystallizing out during this time period.

The last portion of water (35 ml) was added over a period of 1 hour. The sample was then agitated for an additional 2 hours. The trifluoroacetic acid was neutralized with concentrated ammonium hydroxide (5.0 ml, 1.35 g $NH_3$, 79 mmol) which was added slowly with cooling of the batch mixture. The batch was then agitated for 1 hour and then the product filtered and washed with about 100 ml of an acetic acid water mixture (1:2 v/v) followed by washing with 100 ml of water. The filter cake was dried to constant weight in vacuo at 35° C. under a slow nitrogen sweep to yield the titled compound in 98.0% purity (HPLC). The level of dimer was <0.2%.

EXAMPLE 2

Preparation of 6(R)-[2-[8(S)-(2,2-dimethylbutyryloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

Ammonium 7-[1,2,6,7,8,8a(R)-hexahydro-2(S),-6(R)-dimethyl-8(S)-(2,2-dimethylbutyryloxy)-1(S)-naphthyl]-3(R),5(R)-dihydroxyheptanoate (12.5 g, 95.4 wt. % purity by HPLC, 27.6 mmol), and BHA (butylated hydroxy anisole) (0.075 g) were suspended in a mixture of acetic acid (40 ml) and water (20 ml) at 22°-25° C.

under nitrogen. MSA (methanesulfonic acid) (2.94 g, 2.00 ml, 30.6 mmol) was added to the above suspension.

After 2 hours, water (10 ml) was added in one portion. From that point on, the addition of the second portion of water (15 ml) was carried out uniformly over a period of 3 hours. The last portion of water (35 ml) was added over a period of 1 hour, and the sample agitated for an additional hour. The methanesulfonic acid was neutralized with concentrated ammonium hydroxide (4.0 ml, 1.35 g $NH_3$, 63.2 mmol) which was added slowly with cooling of the batch mixture. The batch was then agitated for 1 hour, and then the product filtered and washed with about 100 ml of an acetic acid-water mixture (1:2 v/v) followed by washing with 100 ml of water. The filter cake was dried to constant weight in vacuo at 35° C. under a slow nitrogen sweep to yield the titled compound in 96.5% purity (HPLC). The level of dimer was <0.2%.

EXAMPLE 3

Preparation of 6(R)-[2[8(S)-(2-methylbutyryloxy)-2(S),6(R)-dimethyl-1,2,6,7,8,8a(R)-hexahydronaphthyl-1(S)]ethyl]-4(R)-hydroxy--3,4,5,6-tetrahydro-2H-pyran-2-one The titled compound is prepared following the procedure of Example 1 or Example 2 but substituting Ammonium 7-[1,2,6,7,8,8a(R)-hexahydro-2(S),6(R)-dimethyl-8(S)-(2-methylbutyryloxy) 1(S)-naphty]-3(R),5(R)-dihydroxyheptanoate as the substance to be lactonized. Alternatively acetone or acetonitrile may be substituted as the organic solvent, but with a neutral solvent, the acid is neutralized in the presence of a pH probe to pH 6.

What is claimed is:

1. A process for the lactonization of a compound of structure (I):

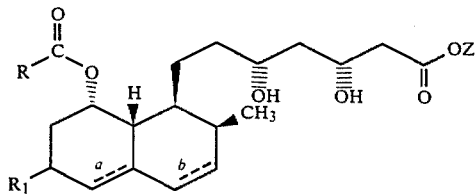

wherein:
R is $C_{1-10}$ alkyl;
$R_1$ is $CH_3$, $CH_2OH$,

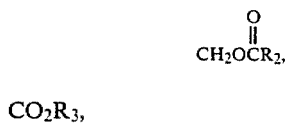

$CO_2R_3$, $$\underset{\underset{O}{\parallel}}{C}NR_4R_5.$$

OH, $CH_2OR_2$, or $CH_2NR_4R_5$;
Z is H or $NH_4+$ or a metal cation;
$R_2$ is $C_{1-5}$ alkyl;
$R_3$ is H or $C_{1-5}$ alkyl;
$R_4$ and $R_5$ are independently selected from H or $C_{1-5}$ alkyl;
a and b are both double bonds or one of a and b is a single bond or both a and b are single bonds; which comprises:
(A) treating (I) with a mixture of a water miscible organic solvent, water and an acid catalyst under an inert gas atmosphere for about 2-3 hours at 20°-25° C.;
(B) treatment of the reaction mixture with additional water to precipitate the product lactone (II) as a crystalline mass.

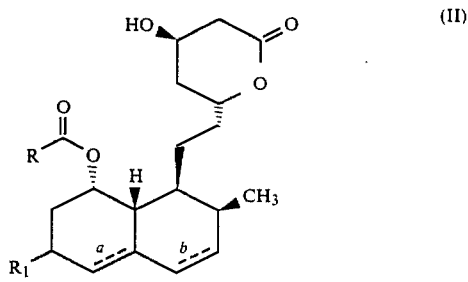

2. A process according to claim 1 wherein:
R is $C_{1-10}$ alkyl,
$R_1$ is $CH_3$; and
Z is H+ or $NH_4+$.

3. A process according to claim 2 wherein R is sec-butyl or 1,1-dimethylpropyl, and a and b are double bonds.

4. A process according to claim 3 wherein: the organic solvent is selected from acetic acid, acetonitrile or acetone.

5. A process according to claim 4 wherein the acid catalyst is selected from: formic, phosphoric, trifluoroacetic, sulfuric, hydrochloric, perchloric, p-toluenesulfonic and methanesulfonic acid.

6. A process according to claim 5 wherein R is 1,1-dimethylpropyl.

7. A process according to claim 6 wherein the organic solvent is acetic acid and Z is $NH_4+$.

8. A process according to claim 7 wherein the acid catalyst is trifluoroacetic acid, or methanesulfonic acid.

9. A process according to claim 8 wherein the acid catalyst is methanesulfonic acid.

10. A process according to claim 5 wherein R is sec-butyl.

11. A process according to claim 10 wherein the acid catalyst is trifluoracetic acid or methanesulfonic acid.

* * * * *